United States Patent
Kshirsagar et al.

(10) Patent No.: US 12,119,107 B2
(45) Date of Patent: Oct. 15, 2024

(54) AI SYSTEM FOR PREDICTING READING TIME AND READING COMPLEXITY FOR REVIEWING 2D/3D BREAST IMAGES

(71) Applicant: Hologic, Inc., Marlborough, MA (US)

(72) Inventors: Ashwini Kshirsagar, Santa Clara, CA (US); Haili Chui, Santa Clara, CA (US); Nikolaos Gkanatsios, Danbury, CT (US); Adora Dsouza, Sunnyvale, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/319,727

(22) Filed: May 18, 2023

(65) Prior Publication Data

US 2024/0021297 A1    Jan. 18, 2024

Related U.S. Application Data

(63) Continuation of application No. 17/033,372, filed on Sep. 25, 2020, now Pat. No. 11,694,792.

(Continued)

(51) Int. Cl.
*G16H 40/20*     (2018.01)
*G06Q 10/0631*   (2023.01)
(Continued)

(52) U.S. Cl.
CPC ....... *G16H 40/20* (2018.01); *G06Q 10/06311* (2013.01); *G06Q 10/06398* (2013.01);
(Continued)

(58) Field of Classification Search
CPC ........ G16H 30/40; G16H 40/20; G16H 50/20; G06T 2207/30004; G06T 2207/10116;
(Continued)

(56) References Cited

U.S. PATENT DOCUMENTS

| 4,821,727 A | 4/1989 | Levene et al. |
| 4,907,156 A | 6/1990 | Doi et al. |

(Continued)

FOREIGN PATENT DOCUMENTS

| CN | 202161328 | 3/2012 |
| CN | 102429678 | 5/2012 |

(Continued)

OTHER PUBLICATIONS

"Filtered Back Projection", (NYGREN), published May 8, 2007, URL: http://web.archive.org/web/19991010131715/http://www.owlnet.rice.edu/~elec539/Projects97/cult/node2.html, 2 pgs.

(Continued)

*Primary Examiner* — Aaron W Carter
*Assistant Examiner* — Courtney Joan Nelson
(74) *Attorney, Agent, or Firm* — Merchant & Gould P.C.

(57) ABSTRACT

Examples of the present disclosure describe systems and methods for predicting the reading time and/or reading complexity of a breast image. In aspects, a first set of data relating to the reading time of breast images may be collected from one or more data sources, such as image acquisition workstations, image review workstations, and healthcare professional profile data. The first set of data may be used to train a predictive model to predict/estimate an expected reading time and/or an expected reading complexity for various breast images. Subsequently, a second set of data comprising at least one breast image may be provided as input to the trained predictive model. The trained predictive model may output an estimated reading time and/or reading complexity for the breast image. The output of the trained predictive model may be used to prioritize mammographic studies or optimize the utilization of available time for radiologists.

20 Claims, 7 Drawing Sheets

Related U.S. Application Data

(60) Provisional application No. 62/907,257, filed on Sep. 27, 2019.

(51) Int. Cl.
| | |
|---|---|
| *G06Q 10/0639* | (2023.01) |
| *G06Q 10/1093* | (2023.01) |
| *G06T 7/00* | (2017.01) |
| *G16H 10/20* | (2018.01) |
| *G16H 30/20* | (2018.01) |
| *G16H 30/40* | (2018.01) |
| *G16H 50/20* | (2018.01) |
| *G16H 50/30* | (2018.01) |

(52) U.S. Cl.
CPC ....... *G06Q 10/1097* (2013.01); *G06T 7/0012* (2013.01); *G16H 10/20* (2018.01); *G16H 30/20* (2018.01); *G16H 30/40* (2018.01); *G16H 50/20* (2018.01); *G16H 50/30* (2018.01); *G06T 2200/24* (2013.01); *G06T 2207/20081* (2013.01); *G06T 2207/30068* (2013.01)

(58) Field of Classification Search
CPC . G06T 2207/20081; G06T 2207/20084; G06T 7/0012; G06T 2210/41; G06V 10/82; G06V 10/44; G06Q 10/06; G06Q 10/06311; G06Q 10/063112; G06Q 10/0633
See application file for complete search history.

(56) References Cited

U.S. PATENT DOCUMENTS

| | | |
|---|---|---|
| 5,078,142 A | 1/1992 | Siczek et al. |
| 5,129,911 A | 7/1992 | Siczek et al. |
| 5,133,020 A | 7/1992 | Giger et al. |
| 5,219,351 A | 6/1993 | Teubner |
| 5,240,011 A | 8/1993 | Assa |
| 5,280,427 A | 1/1994 | Magnusson |
| 5,289,520 A | 2/1994 | Pellegrino et al. |
| 5,343,390 A | 8/1994 | Doi et al. |
| 5,386,447 A | 1/1995 | Siczek |
| 5,415,169 A | 5/1995 | Siczek et al. |
| 5,426,685 A | 6/1995 | Pellegrino et al. |
| 5,491,627 A | 2/1996 | Zhang et al. |
| 5,594,769 A | 1/1997 | Pellegrino et al. |
| 5,609,152 A | 3/1997 | Pellegrino et al. |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,872,828 A | 2/1999 | Niklason et al. |
| 6,022,325 A | 2/2000 | Siczek et al. |
| 6,101,236 A | 8/2000 | Wang et al. |
| 6,102,866 A | 8/2000 | Nields et al. |
| 6,245,028 B1 | 6/2001 | Furst et al. |
| 6,293,282 B1 | 9/2001 | Lemelson |
| 6,459,925 B1 | 10/2002 | Nields et al. |
| 6,468,226 B1 | 10/2002 | McIntyre, IV |
| 6,480,565 B1 | 11/2002 | Ning |
| 6,620,111 B2 | 9/2003 | Stephens et al. |
| 6,626,849 B2 | 9/2003 | Huitema et al. |
| 6,638,235 B2 | 10/2003 | Miller et al. |
| 6,683,934 B1 | 1/2004 | Zhao |
| 6,758,824 B1 | 7/2004 | Miller et al. |
| 6,987,331 B2 | 1/2006 | Koeppe |
| 7,123,684 B2 | 10/2006 | Jing et al. |
| 7,245,694 B2 | 7/2007 | Jing et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,634,050 B2 | 12/2009 | Muller et al. |
| 7,697,660 B2 | 4/2010 | Ning |
| 7,702,142 B2 | 4/2010 | Ren et al. |
| 7,760,924 B2 | 7/2010 | Ruth et al. |
| 7,787,936 B2 | 8/2010 | Kressy |
| 7,831,296 B2 | 11/2010 | DeFreitas et al. |
| 7,869,563 B2 | 1/2011 | DeFreitas |
| 7,889,896 B2 * | 2/2011 | Roehrig ............... G16H 30/20 382/128 |
| 7,991,106 B2 | 8/2011 | Ren et al. |
| 8,532,745 B2 | 9/2013 | DeFreitas et al. |
| 8,594,274 B2 | 11/2013 | Hoernig et al. |
| 9,020,579 B2 | 4/2015 | Smith |
| 9,901,309 B2 | 2/2018 | DeFreitas et al. |
| 10,092,358 B2 | 10/2018 | DeFreitas |
| 10,335,094 B2 | 7/2019 | DeFreitas |
| 10,357,211 B2 | 7/2019 | Smith |
| 10,456,213 B2 | 10/2019 | DeFreitas |
| 10,595,954 B2 | 3/2020 | DeFreitas |
| 2001/0038681 A1 | 11/2001 | Stanton et al. |
| 2002/0113681 A1 | 8/2002 | Byram |
| 2002/0122533 A1 | 9/2002 | Marie et al. |
| 2003/0018272 A1 | 1/2003 | Treado et al. |
| 2003/0073895 A1 | 4/2003 | Nields et al. |
| 2003/0135115 A1 | 7/2003 | Burdette et al. |
| 2004/0077938 A1 | 4/2004 | Mark et al. |
| 2004/0081273 A1 | 4/2004 | Ning |
| 2004/0101095 A1 | 5/2004 | Jing |
| 2004/0127789 A1 | 7/2004 | Ogawa |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0020903 A1 | 1/2005 | Krishnan et al. |
| 2005/0049497 A1 | 3/2005 | Krishnan et al. |
| 2005/0049521 A1 | 3/2005 | Miller et al. |
| 2005/0084060 A1 | 4/2005 | Seppi et al. |
| 2005/0089205 A1 | 4/2005 | Kapur |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2006/0009693 A1 | 1/2006 | Hanover et al. |
| 2006/0025680 A1 | 2/2006 | Jeune-Iomme |
| 2006/0030784 A1 | 2/2006 | Miller et al. |
| 2006/0098855 A1 | 5/2006 | Gkanatsios et al. |
| 2006/0126794 A1 | 6/2006 | Hermann |
| 2006/0129062 A1 | 6/2006 | Nicoson et al. |
| 2006/0155209 A1 | 7/2006 | Miller et al. |
| 2006/0257009 A1 | 11/2006 | Wang |
| 2006/0269040 A1 | 11/2006 | Mertelmeier |
| 2007/0019846 A1 | 1/2007 | Bullitt et al. |
| 2007/0114424 A1 | 5/2007 | Danielsson et al. |
| 2007/0225600 A1 | 9/2007 | Weibrecht et al. |
| 2007/0263765 A1 | 11/2007 | Wu Tao |
| 2008/0019581 A1 | 1/2008 | Gkanatsios et al. |
| 2008/0045833 A1 | 2/2008 | DeFreitas et al. |
| 2008/0101537 A1 | 5/2008 | Sendai |
| 2008/0103834 A1 | 5/2008 | Reiner |
| 2008/0152086 A1 | 6/2008 | Hall |
| 2008/0187095 A1 | 8/2008 | Boone et al. |
| 2008/0198966 A1 | 8/2008 | Hjarn |
| 2009/0003519 A1 | 1/2009 | DeFreitas |
| 2009/0080604 A1 | 3/2009 | Shores et al. |
| 2009/0143674 A1 | 6/2009 | Nields |
| 2009/0171244 A1 | 7/2009 | Ning |
| 2009/0177495 A1 | 7/2009 | Abousy et al. |
| 2009/0296882 A1 | 12/2009 | Gkanatsios et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1 | 6/2010 | Navab |
| 2010/0208037 A1 | 8/2010 | Sendai |
| 2011/0019891 A1 | 1/2011 | Puong |
| 2011/0069808 A1 | 3/2011 | Defreitas et al. |
| 2011/0087132 A1 | 4/2011 | DeFreitas et al. |
| 2011/0110576 A1 | 5/2011 | Kreeger |
| 2011/0182402 A1 | 7/2011 | Partain |
| 2011/0237927 A1 | 9/2011 | Brooks et al. |
| 2011/0257919 A1 | 10/2011 | Reiner |

(56) References Cited

U.S. PATENT DOCUMENTS

| | | |
|---|---|---|
| 2011/0268339 A1 | 11/2011 | Volokh |
| 2012/0014504 A1 | 1/2012 | Jang |
| 2012/0134464 A1 | 5/2012 | Hoernig et al. |
| 2012/0238870 A1 | 9/2012 | Smith et al. |
| 2013/0022165 A1 | 1/2013 | Jang |
| 2013/0044861 A1 | 2/2013 | Muller |
| 2013/0108138 A1 | 5/2013 | Nakayama |
| 2013/0259193 A1 | 10/2013 | Packard |
| 2014/0064444 A1* | 3/2014 | Oh ................... A61B 6/545 378/54 |
| 2014/0073913 A1 | 3/2014 | DeFreitas et al. |
| 2014/0328530 A1 | 11/2014 | Lee |
| 2015/0199478 A1 | 7/2015 | Bhatia et al. |
| 2015/0245817 A1 | 9/2015 | Stone |
| 2015/0347693 A1* | 12/2015 | Lam ................... G16H 40/20 705/3 |
| 2015/0375399 A1 | 12/2015 | Chiu |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0074012 A1 | 3/2016 | Forzoni |
| 2016/0166217 A1 | 6/2016 | Davis |
| 2016/0216769 A1 | 7/2016 | Goetz |
| 2016/0235379 A1 | 8/2016 | Homann |
| 2016/0235380 A1 | 8/2016 | Smith |
| 2017/0251991 A1 | 9/2017 | Wang |
| 2017/0364645 A1* | 12/2017 | Jester ................ G06F 3/04842 |
| 2018/0068066 A1 | 3/2018 | Bronkalla |
| 2018/0256118 A1 | 9/2018 | DeFreitas |
| 2018/0286504 A1* | 10/2018 | Trovato ............. G16H 30/20 |
| 2019/0015058 A1 | 1/2019 | Alamo Valenzuela |
| 2019/0015173 A1 | 1/2019 | DeFreitas |
| 2019/0064929 A1 | 2/2019 | Tomeh |
| 2019/0138693 A1 | 5/2019 | Muller et al. |
| 2019/0188848 A1 | 6/2019 | Madani et al. |
| 2019/0221304 A1 | 7/2019 | Ionasec |
| 2019/0290221 A1 | 9/2019 | Smith |
| 2019/0295248 A1 | 9/2019 | Nakamura et al. |
| 2020/0043600 A1 | 2/2020 | Glottmann et al. |
| 2020/0046303 A1 | 2/2020 | DeFreitas |
| 2020/0093562 A1 | 3/2020 | DeFreitas |
| 2020/0160510 A1 | 5/2020 | Lindemer |
| 2020/0167920 A1 | 5/2020 | Hall et al. |
| 2020/0205928 A1 | 7/2020 | DeFreitas |
| 2020/0286613 A1 | 9/2020 | Rego |
| 2020/0311938 A1 | 10/2020 | Vincent |
| 2020/0357118 A1 | 11/2020 | Yao |
| 2020/0381125 A1 | 12/2020 | Hao et al. |
| 2020/0390404 A1 | 12/2020 | DeFreitas |
| 2021/0000553 A1 | 1/2021 | St. Pierre |
| 2021/0030366 A1 | 2/2021 | Chen |
| 2021/0035680 A1 | 2/2021 | Chen |
| 2021/0098120 A1 | 4/2021 | Kshirsagar |
| 2021/0100626 A1 | 4/2021 | St. Pierre |
| 2021/0303078 A1 | 9/2021 | Wells |
| 2022/0133258 A1 | 5/2022 | Yin et al. |
| 2022/0164586 A1 | 5/2022 | Chui |
| 2022/0164951 A1 | 5/2022 | Chui |
| 2023/0098785 A1 | 3/2023 | St. Pierre |

FOREIGN PATENT DOCUMENTS

| | | |
|---|---|---|
| CN | 108140425 | 6/2018 |
| CN | 108492874 | 9/2018 |
| DE | 102011087127 | 5/2013 |
| EP | 1428473 | 6/2004 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2003-531516 | 10/2003 |
| JP | 2006-519634 | 8/2006 |
| JP | 2007-130487 | 5/2007 |
| JP | 2009-522005 | 6/2009 |
| JP | 2009-157527 | 7/2009 |
| JP | 2009-526618 | 7/2009 |
| JP | 2010-137004 | 6/2010 |
| JP | 2012-501750 | 1/2012 |
| JP | 2014-507250 | 3/2014 |
| JP | 2015-506794 | 3/2015 |
| JP | 2016-035739 | 3/2016 |
| WO | 93/17620 | 9/1993 |
| WO | 94/06352 | 3/1994 |
| WO | 1997/00649 | 1/1997 |
| WO | 00/51484 | 9/2000 |
| WO | 0154463 | 7/2001 |
| WO | 2005/052838 | 6/2005 |
| WO | 2005/079306 | 9/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008/054436 | 5/2008 |
| WO | 2009/026587 | 2/2009 |
| WO | 2010/028208 | 3/2010 |
| WO | 2011/043838 | 4/2011 |
| WO | 2011/063530 | 6/2011 |
| WO | 2012/001572 | 1/2012 |
| WO | 2012/068373 | 5/2012 |
| WO | 2012/112627 | 8/2012 |
| WO | 2012/122399 | 9/2012 |
| WO | 2013/001439 | 1/2013 |
| WO | 2013/078476 | 5/2013 |
| WO | 2013/123091 | 8/2013 |
| WO | 2014/194171 | 12/2014 |
| WO | 2015/061582 | 4/2015 |
| WO | 2016/103094 | 6/2016 |
| WO | 2016/184746 | 11/2016 |
| WO | 2017/058848 | 4/2017 |
| WO | WO-2017218773 A1 * | 12/2017 ......... G06K 9/00469 |
| WO | 2019/030410 | 2/2019 |
| WO | 2016/057960 | 5/2019 |
| WO | 2019/091807 | 5/2019 |
| WO | 2019/102917 | 5/2019 |
| WO | 2019/227042 | 11/2019 |
| WO | 2018/221689 | 4/2020 |
| WO | 2020/216307 | 10/2020 |
| WO | 2021/168281 | 8/2021 |
| WO | 2021/195370 | 9/2021 |

OTHER PUBLICATIONS

"Supersonic to feature Aixplorer Ultimate at ECR", AuntiMinnie. com, 3 pages (Feb. 2018).

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Carton, AK, et al., "Dual-energy contrast-enhanced digital breast tomosynthesis—a feasibility study", Br J Radiol. Apr. 2010;83 (988):344-50.

Chen, SC, et al., "Initial clinical experience with contrast-enhanced digital breast tomosynthesis", Acad Radio. Feb. 2007 14(2):229-38.

Choi Bareum et al., "Surgical-tools detection based on Convolutional Neural Network in laparoscopic robot-assisted surgery", 2017 39th Annual International Conference of the IEEE Engineering in Medicine and Biology Society (EMBC), IEEE, Jul. 11, 2017, pp. 1756-1759.

Diekmann, F., et al., "Digital mammography using iodine-based contrast media: initial clinical experience with dynamic contrast medium enhancement", Invest Radiol 2005; 40:397-404.

(56) References Cited

OTHER PUBLICATIONS

Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Dromain, Clarisse et al., "Dual-energy contrast-enhanced digital mammography: initial clinical results", European Radiology, Sep. 14, 2010, vol. 21, pp. 565-574.
E. Shaw de Paredes et al., "Interventional Breast Procedure", published Sep./Oct. 1998 in Curr Probl Diagn Radiol, pp. 138-184.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Freiherr, G., "Breast tomosynthesis trials show promise", Diagnostic Imaging—San Francisco 2005, V27; N4:42-48.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Giger et al. "Development of a smart workstation for use in mammography", in Proceedings of SPIE, vol. 1445 (1991), p. 101103; 4 pages.
Giger et al., "An Intelligent Workstation for Computer-aided Diagnosis", in RadioGraphics, May 1993, 13:3 pp. 647-656; 10 pages.
Han et al., "MatchNet: Unifying Feature and Metric Learning for Patch-Based Matching", 2015 IEEE Conference on Computer Vision and Pattern Recognition (CVPR), Boston, MA, 2015, pp. 3279-3286.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Jochelson, M., et al., "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, et al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin, JM, et al., Dual-energy contrast-enhanced digital subtraction mammography: feasibility. Radiology 2003; 229:261-268.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
PCT International Preliminary Report on Patentability in International Application PCT/US2020/052895, mailed Apr. 7, 2022, 11 pages.
PCT International Search Report and Written Opinion in International Application PCT/US2020/052895, mailed Sep. 25, 2020, 17 pages.
Poplack, SP, et al, Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Yuan, Yading et al., "Correlative feature analysis on FFDM", Medical Physics, vol. 35, No. 12, Nov. 13, 2008, pp. 5492-5494.
Bouget, David, et al., "Vision-based and marker-less surgical tool detection and tracking: a review of the literature", Medical Image Analysis, published Sep. 13, 2016, DOI:https://doi.org/10.1016/j.media.2016.09.003, 29 pages.

\* cited by examiner

AI SYSTEM FOR PREDICTING READING TIME AND READING COMPLEXITY FOR REVIEWING 2D/3D BREAST IMAGES

CROSS-REFERENCE TO RELATED APPLICATIONS

This application is a continuation of application Ser. No. 17/033,372, now U.S. Pat. No. 11,694,792, filed Sep. 25, 2020, which claims priority to provisional application Ser. No. 62/907,257, filed Sep. 27, 2019, entitled "A1 SYSTEM FOR PREDICTING READING TIME AND READING COMPLEXITY FOR REVIEWING 2D/3D BREAST IMAGES," which applications are incorporated herein by reference in their entirety.

BACKGROUND

Modern breast care involves extensive analysis of radiological images. Given the recent advances in radiological imaging, the amount of data radiologists are required to parse through and evaluate is increasing exponentially. This exponential increase in data often causes a large variation in the time to read radiological images. This variability in time is further exacerbated by individual circumstances of the radiologists (e.g., years of experience, areas of expertise, available image reading tools, etc.) as well as the specific contents of the data to be reviewed. As a result, optimally distributing workload (e.g., radiological images) to available radiologists in a screening center has proven challenging.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for predicting reading time and/or complexity of a mammographic exam. In aspects, a first set of data relating to the reading time of mammographic exams may be collected from one or more data sources associated with a healthcare professional, such as image acquisition workstations, image review workstations, healthcare professional profile data, and preexisting patient data. The first set of data may be used to train a predictive model to predict/estimate an expected reading time for various breast images. Subsequently, a second set of data comprising at least one breast image may be provided as input to the trained predictive model. The trained predictive model may output an estimated reading time and/or reading complexity for the breast image. The estimated reading time may be used to prioritize mammographic exams or optimize the utilization of available time for clinical professionals.

Aspects of the present disclosure provide a system comprising: at least one processor; and memory coupled to the at least one processor, the memory comprising computer executable instructions that, when executed by the at least one processor, performs a method comprising: collecting a first set of data, wherein the first set of data comprises: breast image data, user profile data for a reader of the breast image data, and evaluation data for the breast image data; using the first set of data to train a predictive model to predict an expected reading time for the breast image data; collecting a second set of data, wherein the second set of data comprises at least the breast image; applying the second set of data to the trained predictive model; and receiving, from the trained predictive model, an estimated reading time for the breast image.

Aspects of the present disclosure further provide a method comprising: collecting a first set of data, wherein the first set of data comprises: breast image data, user profile data for a reader of the breast image data, and evaluation data for the breast image data; using the first set of data to train a predictive model to predict an expected reading time for the breast image data; collecting a second set of data, wherein the second set of data comprises at least the breast image; applying the second set of data to the trained predictive model; and receiving, from the trained predictive model, an estimated reading time for the breast image.

Aspects of the present disclosure further provide a computer-readable media storing computer executable instructions that when executed cause a computing system to perform a method comprising: collecting a first set of data, wherein the first set of data comprises: breast image data, user profile data for a reader of the breast image data, and evaluation data for the breast image data; using the first set of data to train a predictive model to predict an expected reading time for the breast image data; collecting a second set of data, wherein the second set of data comprises at least the breast image; applying the second set of data to the trained predictive model; and receiving, from the trained predictive model, an estimated reading time for the breast image.

Aspects of the present disclosure provide a system comprising: at least one processor; and memory coupled to the at least one processor, the memory comprising computer executable instructions that, when executed by the at least one processor, performs a method comprising: collecting a set of data, wherein the set of data comprises at least mammography exam data; applying the set of data to a predictive model trained to predict an expected reading time for the mammography exam data; and receiving, from the predictive model, an estimated reading time for the mammography exam data.

Aspects of the present disclosure provide a system comprising: at least one processor; and memory coupled to the at least one processor, the memory comprising computer executable instructions that, when executed by the at least one processor, performs a method comprising: collecting a first set of data, wherein the first set of data comprises: first mammographic exam data for one or more patients; user profile data for one or more mammographic exam readers of the first mammographic exam data; and evaluation data for the one or more mammographic exam readers; updating a case complexity index based on the first set of data, wherein the case complexity index comprises mappings between complexity values and factors affecting an amount of time required to interpret second mammographic exam data; collecting a second set of data, wherein the second set of data comprises the second mammographic exam data; providing the case complexity index and the second set of data to a predictive model, wherein the predictive model is configured to determine a complexity for the second mammographic exam data based on the case complexity index; receiving, from the trained predictive model, an estimated complexity for reading the second mammographic exam data; and displaying the estimated complexity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1:
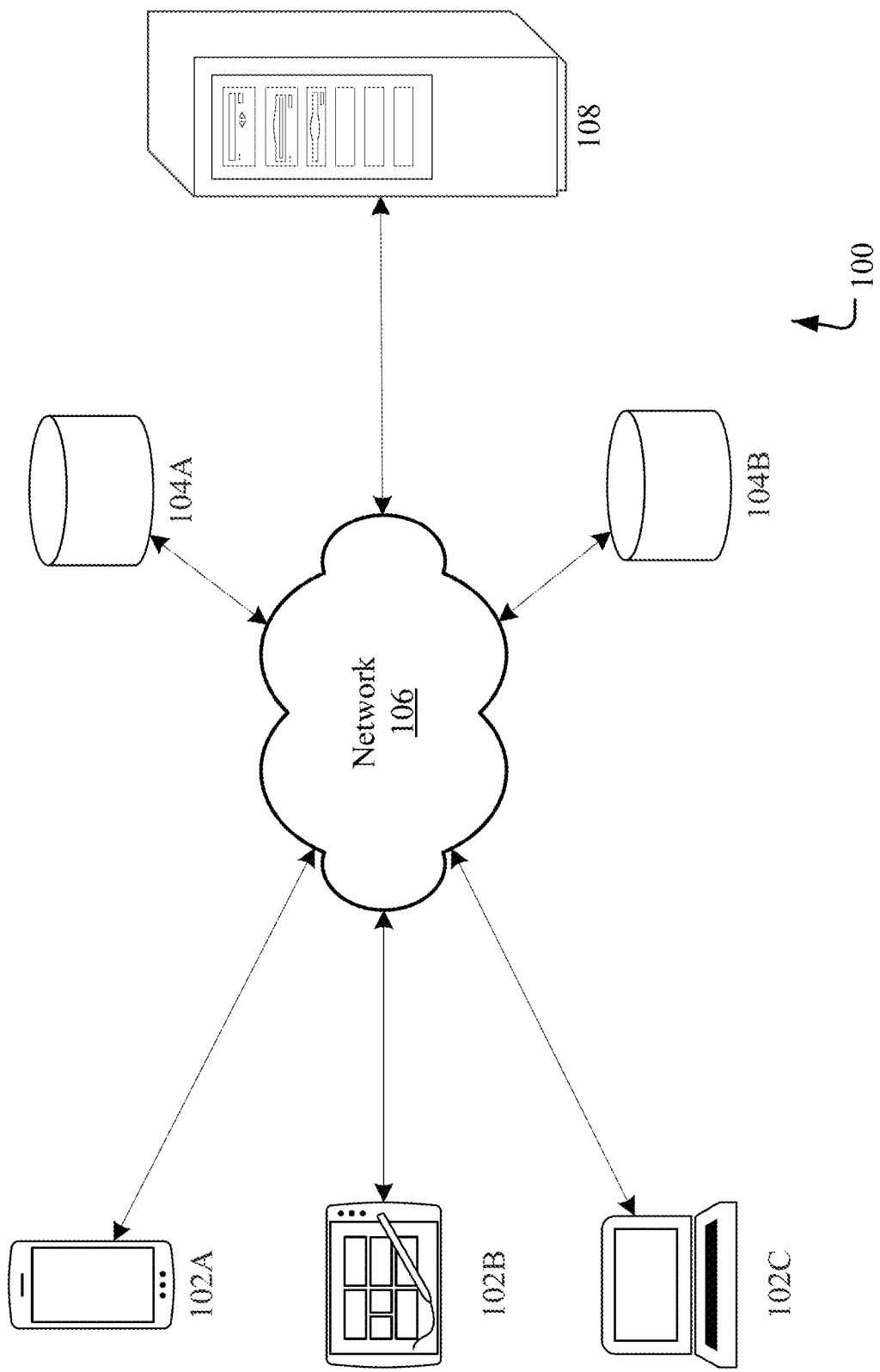
FIG. 1 illustrates an overview of an example system for predicting reading time and/or reading complexity of a mammographic exam, as described herein.

Medical imaging has become a widely used tool for identifying and diagnosing abnormalities, such as cancers or other conditions, within the human body. Medical imaging processes such as mammography and tomosynthesis are particularly useful tools for imaging breasts to screen for, or diagnose, cancer or other lesions with the breasts. Tomosynthesis systems are mammography systems that allow high resolution breast imaging based on limited angle tomosynthesis. Tomosynthesis, generally, produces a plurality of X-ray images, each of discrete layers or slices of the breast, through the entire thickness thereof. In contrast to conventional two-dimensional (2D) mammography systems, a tomosynthesis system acquires a series of X-ray projection images, each projection image obtained at a different angular displacement as the X-ray source moves along a path, such as a circular arc, over the breast. In contrast to conventional computed tomography (CT), tomosynthesis is typically based on projection images obtained at limited angular displacements of the X-ray source around the breast. Tomosynthesis reduces or eliminates the problems caused by tissue overlap and structure noise present in 2D mammography imaging.

In modern breast care centers, the images produced using medical imaging are evaluated by healthcare professionals to determine the optimal breast care path for patients. Due to advances in medical imaging (especially radiological imaging), the accuracy and granularity of information in produced images continue to increase. For example, a larger number of computer-aided detection (CAD) marks identifying image features may be added to an image. Although useful for analytical accuracy, the increased number of identified image features may increase the difficult of reading the image, which increases the time necessary to read the image. Additionally, the advances in medical imaging have resulted in an exponential increase in the volume of data healthcare professionals must review. The coupling of increased image reading complexity and the exponential increase in available data causes a large variation in medical image reading times, which depend upon breast types, the presence of disease and abnormalities, breast density, the image reader's experience, the type of mammographic exam performed, etc. Due to the large variation in medical image reading times, it is often difficult for screening centers to distribute workloads optimally to available radiologists. As a result, many screening centers experience decreased productivity and increased costs.

To address such issues with suboptimal workload distributions, the present disclosure describes systems and methods for predicting reading time and/or reading complexity of a mammographic exam. In aspects, a first set of mammographic exam data relating to one or more 2D and/or 3D breast images and information relating to the readers (human or electronic) of the breast images may be collected from various data sources. Mammographic exam data, as used herein, may refer to information relating to breast image data (e.g., pixel image data and image header data), evaluation data for the breast image data (e.g., study open and close times, reader workload, and reading tools used), user profile-related data for a reader/evaluator of the breast image data (e.g., reader experience, reader expertise, etc.), preexisting patient data (e.g., patient history records/reports and previously collected patient image data), reader opinion data for the breast image data (e.g., reader estimations of reading times or reading complexity), biopsy data, annotations and/or labeled data, and the like. A reader, as used herein, may refer to medical or clinical professional who is trained to review a mammographic exam. Examples of data sources include, but are not limited to, image acquisition workstations, image review workstations, hospital information systems (HISs), patient record systems, reader profile systems, training data repositories, and test/training systems. The first set of mammographic exam data, which may include labeled and/or unlabeled training data, may be used as input to train one or more artificial intelligence (AI) models. A model, as used herein, may refer to a predictive or statistical utility or program that may be used to determine a probability distribution over one or more character sequences, classes, objects, result sets or events, and/or to predict a response value from one or more predictors. A model may be based on, or incorporate, one or more rule sets, machine learning (ML), a neural network, or the like.

In aspects, a second set of mammographic exam data may be collected from one or more of the various data sources described above and provided to the trained AI model. The second set of mammographic exam data may comprise data that is similar to, or the same as, the first set of mammographic exam data. In some examples, however, the second set of mammographic exam data may not include training data. Based on the second set of mammographic exam data, the trained AI model may produce one or more outputs. Example outputs include, but are not limited to, predicted/estimated reading times for one or more images in the second set of mammographic exam data, a complexity rating for reading an image in the second set of mammographic exam data, and time slot availabilities and/or assignments for one or more radiologists. The complexity rating may indicate the difficulty or complexity of reading a mammographic exam or images thereof. The difficulty or complexity of reading a mammographic exam may be based on factors, such breast type, breast density, number of CAD marks, etc. The complexity rating may infer or be correlated with a time for reading a mammographic exam. For instance, the complexity rating and the reading time for a mammographic exam may be related such that the reading time increases as the complexity rating increases. In some aspects, the one or more outputs of the trained AI model may be provided to one or more healthcare professionals and used to balance or optimize the workloads of available radiologists. The balancing/optimization of the workloads may be performed manually by a healthcare professional, or automatically by the trained AI model.

Accordingly, the present disclosure provides a plurality of technical benefits including, but not limited to: generating automated estimates of time required for reading a mammographic exam, generating automated classifications of mammographic exam complexity, leveraging image reader information (e.g., statistics, experience, and credentials) to estimate medical image reading times, automating optimized workload distribution, automated scheduling of reading of mammographic exams, training predictive models based on subjective reader profile factors and/or reader statistics, and training predictive models based on preexisting patient data.

FIG. 1 illustrates an overview of an example system for predicting reading time and/or reading complexity of a mammographic exam as described herein. Example system 100 as presented is a combination of interdependent components that interact to form an integrated system for predicting reading time and/or complexity of a mammographic exam. Components of the system may be hardware components or software components (e.g., applications, application programming interfaces (APIs), modules, virtual machines, or runtime libraries) implemented on and/or executed by hardware components of the system. System 100 may provide an operating environment for software components to execute according to operating constraints, resources, and facilities of system 100. In one example, the operating environment and/or software components may be provided by a single processing device, as depicted in FIG. 5. In other examples, the operating environment and software components of systems disclosed herein may be distributed across multiple devices. For instance, input may be entered on a client device and information may be processed or accessed using other devices in a network, such as one or more server devices.

As one example, the system 100 may comprise computing devices 102A, 102B, and 102C (collectively, "computing device(s) 102"), processing system 108, and network 106. One of skill in the art will appreciate that the scale of systems such as system 100 may vary and may include more or fewer components than those described in FIG. 1. For instance, in some examples, the functionality and/or data provided by computing device(s) 102 may be integrated into a single computing device or system. Alternately, the functionality and/or data of processing systems 106 and/or 108 may be distributed across multiple systems and devices.

Computing device(s) 102 may be configured to receive mammographic exam data relating to a healthcare patient and/or healthcare professional. The mammographic exam data may be received using one or more user interfaces (e.g., a graphical user interface ("GUI"), command line, menu driven interface, or data feed) or sensors (e.g., microphones, touch-based sensors, keyboards, pointing/selection tools, optical/magnetic scanners, or accelerometers) of computing device(s) 102. Examples of computing device(s) 102 include, but are not limited to, image acquisition systems (e.g., X-ray, ultrasound, and magnetic resonance imaging (MRI) systems), image review workstations, HIS devices, patient record devices, mobile healthcare devices (e.g., wearable devices, mobile phones, and tablets), and devices storing healthcare professional information. Computing device(s) 102 may store the mammographic exam data locally on computing device(s) 102 and/or remotely in one or more data storage locations, such as data stores 104A and 104B (collectively, "data store(s) 104"), via network 106. Computing device(s) 102 and data store(s) 104 may be located in one or more healthcare facilities, in a facility associated with a healthcare facility, or in the possession of a healthcare professional. In examples, the mammographic exam data may be provided to computing device(s) 102 using manual processes, automatic processes, or some combination thereof. For instance, a healthcare professional located at a healthcare facility may manually enter mammographic exam data into one or more computing devices. Alternately, device located remotely from the healthcare facility may automatically upload mammographic exam data to one or more computing devices of the healthcare facility. As a specific example, a computing device located at the residence of a healthcare professional may automatically upload mammographic exam data to a healthcare facility device as part of a daily synchronization process.

Processing system 108 may be configured to train and/or provide a ML model. In aspects, processing system 108 may have access to one or more sources of mammographic exam data, such as computing device(s) 102 and/or data source(s) 104, via network 106. A first set of mammographic exam data may be provided as input to processing system 108. Processing system 108 may use the first set of mammographic exam data to train one or more AI processing components. For example, processing system 108 may train an artificial neural network, a support vector machine (SVM), a linear reinforcement model, a random decision forest, or a similar ML technique. After the AI processing component has been trained, a second set of mammographic exam data may be provided as input to processing system 108. Based on the second set of mammographic exam data, processing system 108 may generate one or more outputs, such as estimated reading times for an image in the second set of mammographic exam data, a complexity rating or label for reading an image in the second set of mammographic exam data, one or more reader-specific estimated reading times, reading complexities, or reading labels, time slot availabilities and/or assignments for one or more radiologists, etc. The outputs may be provided (or made accessible) to other components of system 100, such as computing device(s) 102. In examples, the outputs may be evaluated by one or more healthcare professionals to determine study prioritization and/or optimization of workload distribution.

Figure 2:
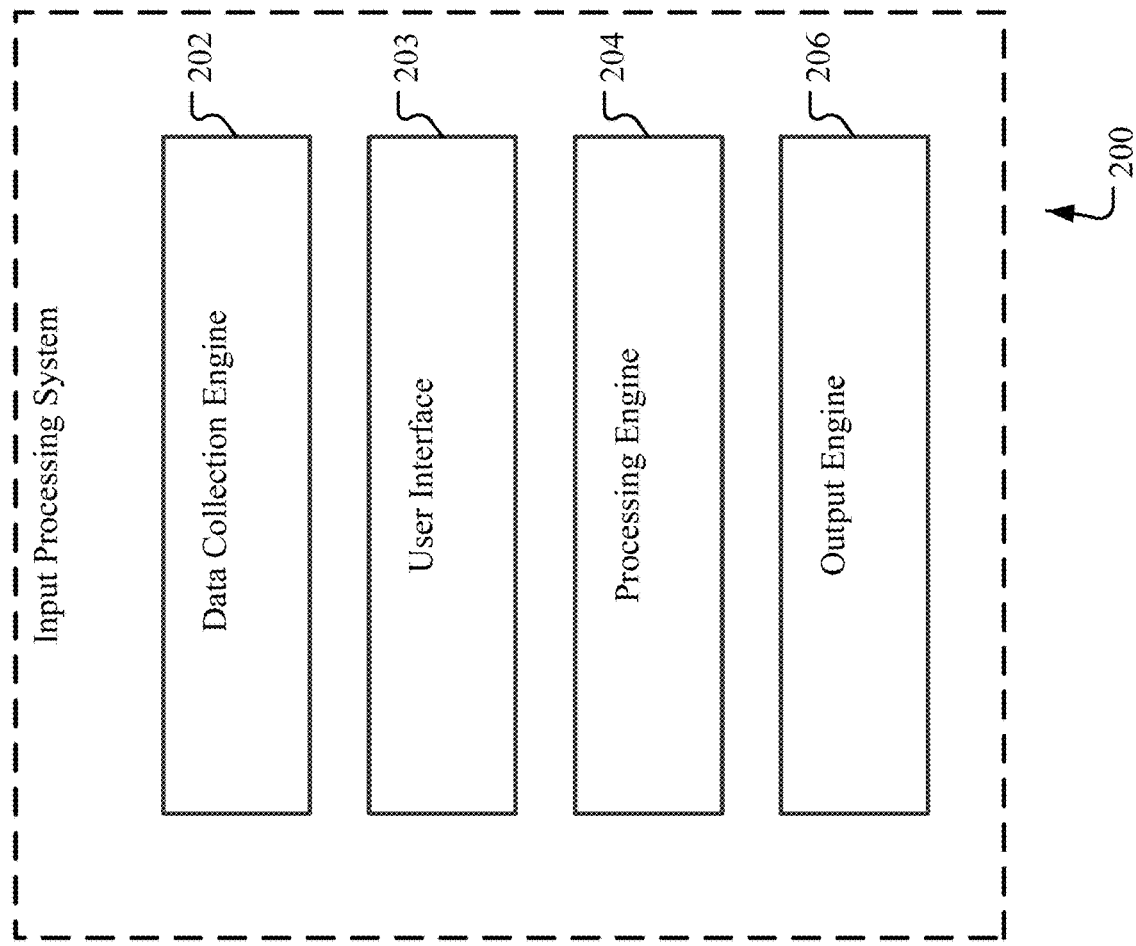
FIG. 2 illustrates an overview of an example input processing system for predicting reading time and/or reading complexity of a mammographic exam, as described herein.

FIG. 2 illustrates an overview of an example input processing system 200 for predicting reading time and/or reading complexity of a mammographic exam, as described herein. The reading prediction techniques implemented by input processing system 200 may comprise the reading prediction techniques and data described in the system of FIG. 1. In some examples, one or more components (or the functionality thereof) of input processing system 200 may be distributed across multiple devices and/or systems. In other examples, a single device may comprise the components of input processing system 200.

With respect to FIG. 2, input processing system 200 may comprise data collection engine 202, processing engine 204, and output engine 206. Data collection engine 202 may be configured to access and/or collect a set of data. In aspects, data collection engine 202 may have access to information relating to one or more 2D/3D breast images and/or relating to the readers/evaluators of the mammographic exam. The information may comprise or represent various types of data, such as text data, speech data, image data, video data, gesture data, etc. At least a portion of the information may be test data or training data that includes labeled data, images, and known mammographic exam reading times. In some examples, the information may be stored in and/or collected from one or more computing devices located in, or accessible to, a healthcare facility or a healthcare professional. The information may include breast image data, evaluation data for the breast image data, user profile-related data for a reader/evaluator of the breast image data, and the like.

In other examples, the information may be collected from a user via an interface, such as user interface 203. User interface 203 may be configured to collect user input from or relating to one or more healthcare professionals. Examples of the user input include identification information, performance statistics, current and/or historic workload information, user estimations of reading times or reading complexities for images or image types, and other user profile-related information. User interface 203 may comprise various user interface elements for collecting the user input and/or navigating or interacting with results provided by user interface 203. As one example, user interface 203 may comprise at least an image data list component, an image data review component, and a self-evaluation component. The image data list component may be configured to display a list of one or more image data file names or identifiers. The image data review component may be configured to provide a preview or view of the image data files provided by the image data list component. The self-evaluation component may be configured to present a set of options that enable a user to provide an estimated reading time or reading complexity for image data files provided by the image data list component. The estimated reading time may represent a reader's opinion of the amount of time required by the reader to read a selected mammographic exam. The estimated reading complexity may represent a reader's opinion of the reading complexity of a selected mammographic exam. The estimated reading complexity may be provided as a label (e.g., easy, medium, hard) or a numerical value (e.g., on a scale of 0-100). Similarly, the estimated reading time may be provided for the reader to select as a label (e.g., fast, medium, slow). Such subjective information, such as the reader's perception of the reading may be used to train the AI processing algorithms or models as described below. Similarly, the subjective information may be used as scores or weights in determining the reading time and/or complexity. For example, for low density, fatty breasts without concerning findings which are less stressful, the perception of reading time may be 'fast', although in reality a reader may have taken additional time to scroll through and assess the mammographic exam.

Processing engine 204 may be configured to process the received information. In aspects, the received information may be provided to processing engine 204. Processing engine 204 may apply one or more AI processing algorithms or models to the received information. For example, processing engine 204 may apply a supervised learning model for classification and regression analysis of the received information. In some aspects, the received information may be used by processing engine 204 (or an alternate component of input processing system 200) to train the AI processing algorithms or models. The trained AI processing algorithms or models may then be used to evaluate received information in order to determine correlations between the received information and the training data used to train the AI processing algorithms or models. The evaluation may include an analysis of various factors that may influence the reading time of an image. Such factors include, but are not limited to, the number of lesions (or abnormalities/concerning findings) detected in the image, the type of anomalies/findings identified by the image, the location of evaluation within the breast (e.g., superior, medial inferior or lateral), the symmetry between a patient's breasts, the number of image slices generated, breast density, breast thickness, breast area, breast tissue composition structure, breast tissue patterns, number of computer-aided detection (CAD) markers, type of image processing used (e.g., artifact reduction, de-noising, etc.), breast positioning parameters of an imaged breast, noise and contrast parameters, type or study performed (e.g., screening, diagnostic, etc.), number of exposures, types of compression paddles used, time of day of the reading, type of workstation and tools used for the reading (e.g., ease of pan/zoom, availability of "smart" hanging protocols, availability of easy annotation tools, availability of tracking, auto-mapping, and "smart" scrolling tools, etc.), reading tool usage (e.g., number of click events, scroll events, and zoom in/out events), user focus data (e.g., dwell time, eye gaze, and hover events), reader experience, reader specialization and training, reader age, reader reading time/complexity opinions or estimates, and reader proficiency.

In some aspects, the various factors analyzed by processing engine 204 may be manually selected or weighted according to one or more criteria, such as user preference. For example, user interface 203 may enable users to select a set of factors to be considered when analyzing received information. The user interface may also enable users to assign importance scores or weights to the set of factors or modify importance scores or weights previously assigned to the set of factors. For example, the self-evaluation component described above may enable a user to assign or modify scores or weights to the set of factors. Further, the self-evaluation component may enable the user to navigate or otherwise interact with set of factors. The scores or weights may indicate the perceived/determined importance of certain factors with respect to other factors. In other aspects, the various factors analyzed by processing engine 204 may be automatically selected or weighted using one or more AI or ML techniques. As one specific example, reader information for one or more readers may be provided to processing engine 204. The reader information may include at least reader experience, previous evaluation data for the reader (e.g., previous reading times), and reader opinions or estimates of reading time and/or reading complexity for one or more images or image types. Based on the provided reader information and/or previous evaluation results, processing engine 204 may determine that the previous reading times and/or reader estimates of reading times for clinical professionals having more experience and more advanced sensitivity and specificity in detecting malignant findings should be given more weight than the same information (e.g., previous reading times and/or reader estimates of reading times) for clinical professionals having less experience. As a result, processing engine 204 may assign higher weights/scores to analyzed factors associated with clinical professionals having more experience. Based on the evaluation of the various factors, processing engine 204 may identify one or more outputs or output categories.

Output engine 206 may be configured to create one or more outputs for the received information. In aspects, output engine 206 may access the outputs or output categories identified by processing engine 204. Based on the identified outputs or output categories, output engine 206 may create one or more outputs. As one example, output engine 206 may generate a predicted reading time for a mammographic exam in the received information based on an analysis by processing engine 204. The predicted reading time may represent an amount of reading time, a range of reading time (e.g., 15-20 minutes), or a reading time category (e.g., Low, Medium, High) that an "average" reader requires to read a mammographic exam. An "average" reader may be classified as a reader having one or more attributes within a specified attribute range. Alternately, the predicted reading time may represent a category or classification (e.g., fast, medium, or slow) indicating the amount of reading time that an average reader requires to read a mammographic exam. For instance, a "fast" category may correspond to reading times under 10 minutes, a "medium" category may correspond to reading times between 10 minutes and 20 minutes, and a "slow" category may correspond to reading times above 20 minutes.

As another example, output engine 206 may generate a predicted reading time for a mammographic exam in which that predicted reading time represents the amount of reading time, a range of reading time, or a reading time category that a specific reader requires to read a mammographic exam. The specific user may be a user currently logged into input processing system 200, a user who has previously logged into input processing system 200, a user selected by a user currently logged into the input processing system 200, a user selected by input processing system 200, or the like. For example, output engine 206 may generate a predicted reading time that is personalized to a user currently logged into input processing system 200. The predicted reading time for the user may be based on user-profile data and/or previous reading time data of the user, which may indicate that the user is a comparatively fast reader. As a result, the predicted reading time for the user may be lower than the predicted reading time for an average reader or a slow reader.

Alternately, output engine 206 may generate multiple predicted reading times. The multiple predicted reading times may correspond to individual readers or categories of readers. For instance, a first reading time may correspond to readers having less than five years of experience, a second reading time may correspond to readers having between five and ten years of experience, and a third reading time may correspond to readers having more than ten years of experience.

As yet another example, output engine 206 may generate a complexity rating for an image in the received information based on a set of factors or a complexity index. The complexity rating may represent the difficulty or complexity of reading a mammographic exam or images thereof for one or more readers. The difficulty or complexity of reading a mammographic exam may be based on objective and/or subjective factors. Examples of objective factors include, but are not limited to, the number and/or type of findings or CAD marks detected in an image, the breast evaluation location, and breast density and tissue composition. Examples of subjective factors include, but are not limited to, reader experience, reader knowledge, reader evaluation technique, and reader competency. In examples, the difficulty or complexity of reading a mammographic exam may increase based on the quantity of factors considered. For instance, an analysis of 3-5 factors may be less complex than an analysis of 10-15 factors. The difficulty or complexity of reading a mammographic exam may also increase based on the values of the factors considered. For instance, the complexity of reading a mammographic exam may increase as the number CAD marks increases, the number CAD marks detected in a specific portion of the breast increases, or the amount of dense breast tissue evaluated increases. The complexity of reading a mammographic exam may also effectively increase for inexperienced readers or less competent readers.

Alternately, output engine 206 may generate multiple complexity ratings. The multiple complexity ratings may correspond to individual readers or categories of readers. For instance, the complexity rating of "difficult" may be assigned to readers having less than five years of experience, and a complexity rating of "moderate" may be assigned to readers having more than five years of experience.

In aspects, the predicted reading time and/or the complexity value may be stored and associated with the mammographic exam associated with the patient. The mammographic exam (or elements thereof) may be provided to one or more destinations, such as a device, an application, or service. The destination(s) may enable a healthcare professional to view and interact with the mammographic exam (including the predicted reading time and/or the complexity value) via, for example, the user interface described above. As a specific example, a reading time and/or the complexity value that has been associated with a specific mammographic exam may be displayed to a reader in a patient worklist for the user. Alternately, the reading time and/or the complexity value may be displayed to a technologist performing the screening or diagnostic scans on the patient(s). In at least one aspect, output engine 206 may also cause one or more additional actions to be performed. For instance, based on the predicted reading time and/or the complexity value, output engine 206 may identify one or more clinical professionals having the expertise and available time to read the mammographic exam. Reading the mammographic exam, as used herein, may refer to various methods and approaches for reviewing and interpreting images and patient information. For example, one reading method may include a reader verifying that images are of satisfactory quality (e.g., no or minimal motion or blurring). If the images (or at least a portion thereof) are of satisfactory quality, the reader may evaluate the size and symmetry of the breasts. The reader may also compare the current images with previously collected images to identify changes between the images. The comparison may include viewing different image views of the breasts, such as mediolateral-oblique, mediolateral, cranial-caudal, etc. The viewings of the image views may be performed in various orders and viewing combinations. The reader may view a 2D image synthesized from two or more tomography images and investigate the CAD marks indicated by the tomography images. The reader may view various features in the images, such as calcifications, areas of skin thickening, features that are associated with types of cancers, speculated masses, etc. The reader may annotate one or more images based on specific areas of interest and determine a finding or a result. The finding or result may then be recorded in a report using standardizes methodology or categories, such as BI-RADS.

In aspects, identify one or more clinical professionals may be accomplished by output engine 206 by querying one or more HIS devices for reader information, such as reading statistics, reader availability, education/expertise, experience, etc. In aspects, a healthcare professional receiving the output of output engine 206 may use the output to balance or optimize the workloads of available clinical professionals. For example, a clinical professional may prefer reading complex mammography exam early in the day, which enables the clinical professional to leave the less complex and/or less time-consuming mammography exam readings for the end of the day. As such, the clinical professional may use the output of output engine 206 to arrange their workload accordingly. As another example, a clinical professional may only have a small time slot available on a particular day. As such, the clinical professional may use the output of output engine 206 to arrange their workload to maximize the number of mammography exam readings that the clinical professional may perform in the time slot.

Alternately, the output may be used to automate the balancing or optimization of the workloads of available clinical professionals. For instance, the output of output engine 206 may be provided to a workload management system/service that is configured to dynamically create/update clinical professional workloads. The workload management system/service may balance the workloads of two clinical professionals such that the first clinical professional is assigned ten mammography exam readings per day, each categorized as having "Fast" reading times, and the second clinical professional is assigned five mammography exam readings per day, each categorized as having "Slow" reading times. Despite the different number of mammography exam readings assigned to the first and second clinical professional, their respective workloads may require approximately the same amount of time to complete. Alternately, the workload management system/service may balance the workloads of two clinical professionals such that each clinical professional is assigned the same number and mix of complex mammography exam readings or such that the clinical professional having the most experience is assigned a proportionately higher number of complex and/or "Slow" reading time mammography exam readings.

Having described various systems that may be employed by the aspects disclosed herein, this disclosure will now describe one or more methods that may be performed by various aspects of the disclosure. In aspects, methods 300 and 400 may be executed by an example system, such as system 100 of FIG. 1 or input processing system 200 of FIG. 2. In examples, methods 300 and 400 may be executed on a device comprising at least one processor configured to store and execute operations, programs, or instructions. However, methods 300 and 400 are not limited to such examples. In other examples, methods 300 and 400 may be performed on an application or service for automating clinical workflow decisions. In at least one example, methods 300 and 400 may be executed (e.g., computer-implemented operations) by one or more components of a distributed network, such as a web service/distributed network service (e.g., cloud service).

Figure 3:
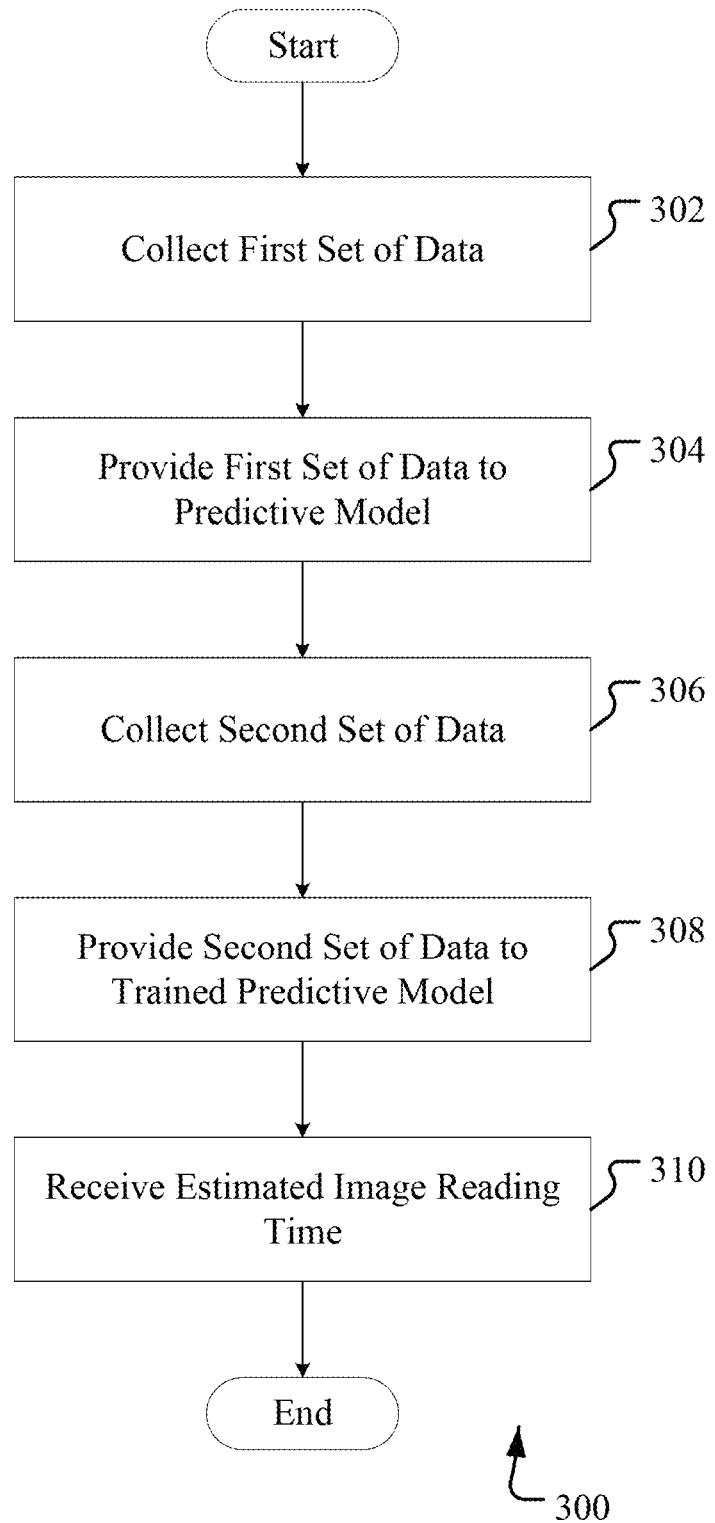
FIG. 3 illustrates an example method for predicting reading time of a mammographic exam, as described herein.

FIG. 3 illustrates an example method 300 for predicting reading time of a mammographic exam as described herein. Example method 300 begins at operation 302, where a first set of data is collected. In aspects, a data collection component, such as data collection engine 202, may collect or receive a first set of data from one or more data sources. The first set of data may comprise or relate to 2D and/or 3D breast image data, image evaluation data, and/or image reader information. In at least one aspect, the first set of data may comprise labeled and/or unlabeled training data. Examples of breast image data may include, but are not limited to, pixel image data and image header data. Pixel image data may be used to derive various attributes of a patient's breast, such as tissue patterns, texture, density, complexity, thickness, volume, and abnormalities. Image header data may provide information such as the type of study (e.g., screening, diagnostic, etc.) performed, the image resolution, the type of hardware system used to collect the images, the image processing method used, etc. Examples of image evaluation data may include, but are not limited to, study (e.g., mammographic exam reading session) open and close times, type of reading tools used (e.g., magnifier, notation tool, measurement tool, etc.), reading tool usage data (as described above with respect to processing engine 204), hanging protocol, workstation hardware/software configuration, study reading times, number and/or type of studies performed, previous patient report data, etc. Examples of image reader information may include, but are not limited to, a reader's experience, expertise, certifications, title/classification, workload/status, proficiency rating, reading time/complexity opinions, and age.

At operation 304, the first set of data is provided to a predictive model. In aspects, one or more portions of the first set of data may be provided to an evaluation component, such as processing engine 204. The evaluation component may be, comprise, or have access to one or more predictive models. The first set of data may be provided as input to a predictive model to train the predictive model to generate one or more outputs. Example outputs include estimated reading times for breast images, complexity ratings for reading breast images, identification of recommended image readers, and time slot availabilities of recommended image readers. In at least one aspect, the first set of data may be used by the evaluation component to generate or update a case complexity index. For example, the evaluation component may use an index creation model or algorithm to generate or update a case complexity index. The case complexity index may comprise a range of complexities associated with reading one or more images or image types. The case complexity index may be configured to provide one or more complexity ratings for an image based on a set of factors that may influence the time required to read the image. In examples, generating or updating a case complexity index may comprise using ML to map a complexity rating to the positive identification of one or more factors, factor values, or a range of factor values. For instance, a rating of "easy" may be mapped to a set of features in which breast density is low and the number of lesions identified in an image is two or fewer. In other examples, the generating or updating a case complexity index may comprise creating complexity rating categories based on scores associated with various factors or factor values. For instance, various factors/attributes associated with a mammographic exam reading may be scored using a scoring model or algorithm. The score for each factor/attribute may be aggregated and used to establish a range of values indicating one or more rating categories. In some aspects, a trained predictive model and/or a case complexity index may be provided to, and/or implemented by, one or more systems or devices.

At operation 306, a second set of data is collected. In aspects, a data collection component, such as data collection engine 202, may collect or receive a second set of data from one or more data sources. The second set of data may comprise at least a portion of data that is similar in type, category, and/or value to the first set of data. For example, the second set of data may comprise or relate to breast image data, image evaluation data, and/or image reader information. In some examples, however, the second set of data may not include labeled or unlabeled training data.

At operation 308, the second set of data is provided to a trained predictive model. In aspects, one or more portions of the second set of data may be provided to an evaluation component, such as processing engine 204. The evaluation component may provide the second set of data to a predictive model, such as the predictive model trained during operation 304. The trained predictive model may evaluate the second set of data to determine correlations between the second set of data and training data used to train the predictive model. For example, based on training data used to train a predictive model, the predictive model may determine that the reading time of breast images having a particular set of breast attributes (e.g., shape, density, lesions, etc.) varies based on the attributes of the image reader and the conditions under which the mammographic exam reading is performed. For instance, the predictive model may identify that images of breasts having an ACR Breast Imaging Reporting and Data System (BI-RADS) mammographic density (MD) of Type 1, and 0-2 lesions generally require image readers having 5 or more years of experience 10 minutes to read in the morning (when the reader is relatively rested), and 15 minutes to read in the evening (when the reader is relatively fatigued). The predictive model may further identify that images of breasts having the above attributes (e.g., MD Type 1, 0-2 lesions detected) generally require: image readers having less than 5 years of experience 25 minutes to read in the morning, and 30 minutes to read in the evening.

In some aspects, the evaluation component may evaluate the second set of data using the case complexity index described above. The evaluation may include identifying, organizing, and/or classifying one or more features or attributes of the second set of data. The identified features/attributes may be compared to, or evaluated against, the case complexity index using decision logic, such as a ML algorithm or a set of evaluation rules. As one example, a predictive model may determine that predicted reading times for breast images of a particular type or having a particular set of attributes are within the 85th percentile for reading time duration (e.g., indicating an increased reading duration as compared to other breast images of image types). Based on the determined percentile rank, the case complexity index may provide an indication that the determined/predicted complexity for such images. For instance, the case complexity index may provide a designation of "difficult" for any breast images determined to be within at least $80^{th}$ percentile. As another example, at least a portion of the data used to determine the predicted reading time (e.g., breast image data, image evaluation data, and/or image reader information) may be evaluated using the case complexity index. The evaluation may include assigning values or scores to features in the data. A scoring engine or algorithm may be applied to the assigned values/scores to generate an aggregated mammographic exam reading score. For instance, data in the second set of data may be featurized and used to construct one or more feature vectors. A feature vector, as used herein, may refer to an n-dimensional vector of numerical features that represent one or more objects. The feature vector(s) may be applied to, or evaluated against, the case complexity index. Based on the feature vector values/scores, the case complexity index may provide a corresponding score or designation indicating the complexity or reading a particular breast image or type of breast image.

At operation 310, an estimated mammographic exam reading time is received. In aspects, the trained predictive model and/or the case complexity index may provide one or more outputs for the second set of data. As discussed in operation 304, the outputs may include estimated mammographic exam reading times, estimated complexity ratings for images to be read, recommendations or assignments of image readers, job/task scheduling dates/time, etc. The output may be provided to one or more HIS devices and/or healthcare professional devices. Based on the output, a reader and/or a reading session time may be manually or automatically assigned for the image(s) in the second set of data. In some aspects, the predictive model output, the case complexity index output, and/or the statistics and parameters of the resulting mammographic exam reading/study, may be provided as input to a predictive model (such as the predictive model described in operations 304 and 308) and/or a component implementing or maintaining the case complexity index. The input may be used to further train the predictive model and/or the case complexity index. As one example, based on the output of a predictive model, an image requiring an estimate reading time of 15 minutes may be assigned to a radiologist having 10 years of experience. The mammographic exam reading/study may actually take the radiologist 25 minutes. The estimate reading time, the actual reading time, and the parameters/conditions of the mammographic exam reading/study (e.g., reading tools used, time of day, radiologist information, etc.) may be provided to the predictive model. The predictive model may use the information to adjust future reading time estimates for the radiologist, or to reevaluate the reading times for images having similar attributes the image in the mammographic exam reading/study.

Figure 4:
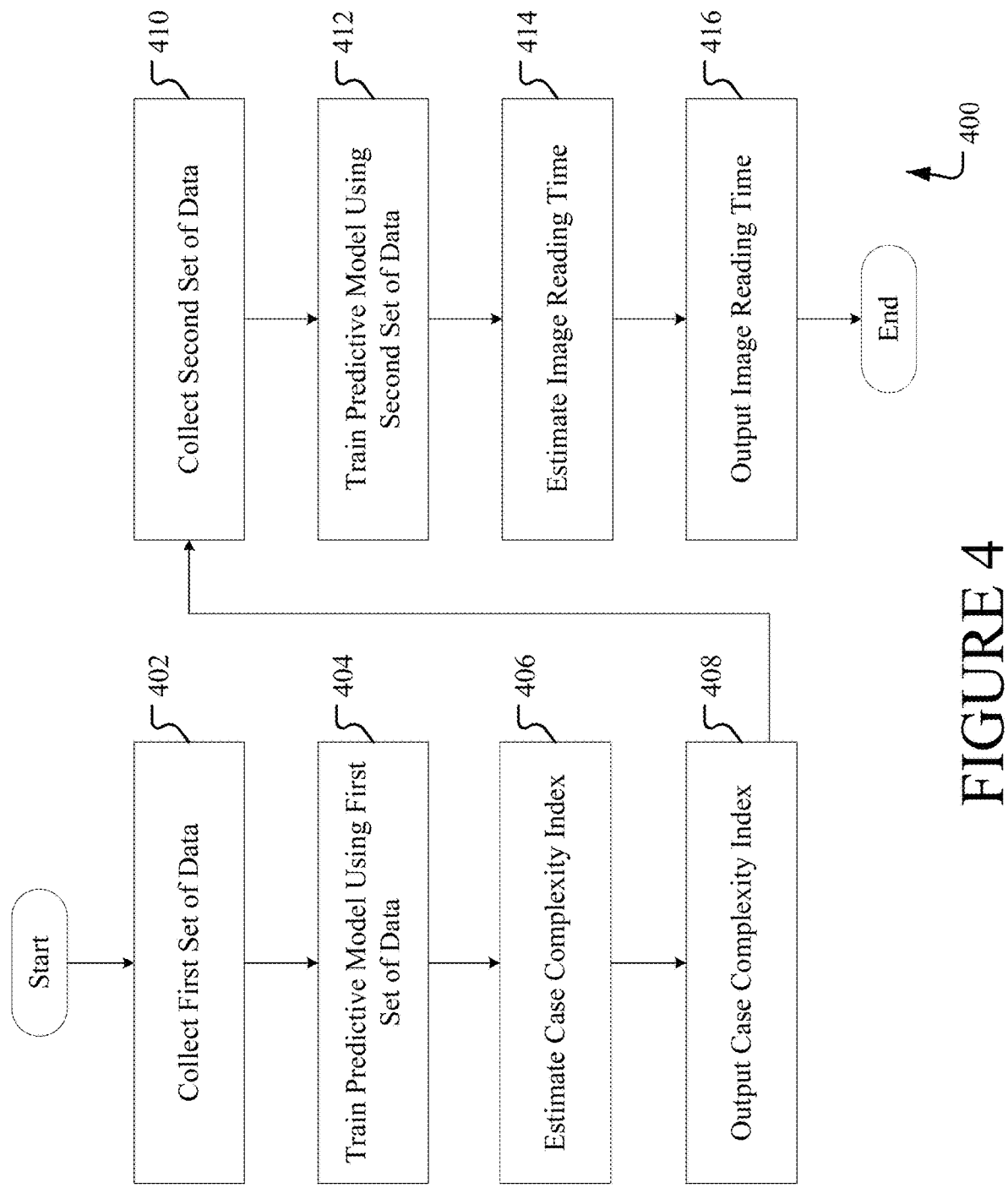
FIG. 4 illustrates an example method for predicting reading complexity and/or reading time of a mammographic exam, as described herein.

FIG. 4 illustrates an example method 400 for predicting reading complexity and/or reading time of a mammographic exam as described herein. Example method 400 begins at operation 402, where a first set of data is collected. In aspects, a data collection component, such as data collection engine 202, may collect or receive a first set of data from one or more data sources. The first set of data may comprise or relate to 2D and/or 3D breast image data, image evaluation data, and/or image reader information. In at least one aspect, the first set of data may comprise labeled and/or unlabeled training data. Examples of breast image data may include, but are not limited to, pixel image data and image header data. Pixel image data may be used to derive various attributes of a patient's breast, such as tissue patterns, density, complexity, thickness, volume, and abnormalities. Image header data may provide information such as the type of study (e.g., screening, diagnostic, etc.) performed, the image resolution, the type of hardware system used to collect the images, the image processing method used, etc. Examples of image evaluation data may include, but are not limited to, study (e.g., mammographic exam reading session) open and close times, type of reading tools used (e.g., magnifier, notation tool, measurement tool, etc.), hanging protocol, workstation hardware/software configuration, study reading times, number and/or type of studies performed, previous patient report data, etc. Examples of image reader information may include, but are not limited to, a reader's experience, expertise, certifications, title/classification, workload/status, proficiency rating, and age.

At operation 404, a predictive model is trained using the first set of data. In aspects, the first set of data may be provided to an evaluation component, such as processing engine 204. The evaluation component may be, comprise, or have access to one or more predictive models. The first set of data may be provided as input to a predictive model to train the predictive model to generate one or more outputs. Example outputs include estimated complexity ratings or a complexity system/component for reading or interpreting mammographic exam data. As a particular example, the first set of data may comprise a labeled or annotated breast image, a reported amount of time for reading the image, a reported or suggested complexity rating for reading the image, and profile information for the reader of the image. The first set of data may be provided to a predictive model. The predictive model may use one or more data correlation techniques to determine correlations between the reported/suggested complexity rating and the other factors/data points in the first set of data.

At operation 406, a case complexity index may be estimated. In aspects, a predictive model may use the first set of data to estimate or update a case complexity index. A case complexity index, as used herein, may refer to a data structure or component comprising mappings of complexity values or labels to data/factors that may influence the amount of time required to read or interpret a mammographic exam. Estimating or updating the case complexity index may comprise using an index creation algorithm, a data mapping utility, or data correlation algorithm. The case complexity index may be configured to provide one or more complexity ratings or labels for collected mammographic exam data based on a set of factors or data points associated with the collected mammographic exam data. In examples, the set of factors or data points may influence the time required to read the collected breast image. For instance, a rating of "2" on a scale of 1 to 5 (where "1" is very easy, "2" is easy, "3" is moderate, "4" is difficult, and "5" is very difficult) may be mapped to a set of features in which at least two of the following factors is satisfied: breast density is low, the number of lesions identified in an image is one or fewer, and a reader has more than 10 years of experience.

At operation 408, the case complexity index may be output. In aspects, an estimated/updated case complexity index may be output by a predictive model or the evaluation component. The case complexity index that is output may be a standalone executable file or utility. Alternatively, the output case complexity index may be integrated into a service, application, or system. As one example, the case complexity index (or an instance thereof) may be distributed to and integrated into a user interface of one or more workstations (e.g., image acquisition workstations, image review workstations, other HIS computing devices, etc.). The user interface many enable a healthcare professional to evaluate and/or modify the mappings, mapping logic, classifications, and/or category values of the case complexity index. The user interface may additionally enable a healthcare professional to assign a weighted value or importance to various factors evaluated by the case complexity index. For instance, a healthcare professional that is more interested in the number of lesions identified in a breast image than breast density, may assign a higher importance to the number of identified lesions. Assigning a higher importance may include applying a multiplier (such as ×1.25) to factors relating to the number of identified lesions, or setting a designation for a particular value range (e.g., mapping "0" lesions to "very easy," "1-2" lesions to "easy," etc.).

At operation 410, a second set of data is collected. In aspects, a data collection component, such as data collection engine 202, may collect or receive a second set of data from one or more data sources. The second set of data may comprise at least a portion of data that is similar in type, category, and/or value to the first set of data. For example, the second set of data may comprise or relate to breast image data, image evaluation data, and/or image reader information. In some examples, however, the second set of data may not include labeled or unlabeled training data.

At operation 412, a predictive model is trained using the second set of data. In aspects, the second set of data and/or data relating to the case complexity index may be provided to an evaluation component, such as processing engine 204. The evaluation component may use the provided information to train a predictive model. In some examples, the predictive model may be the predictive model trained at operation 404. In other examples, a new or an alternate predictive model may be trained. The predictive model may be trained to generate one or more outputs. Example outputs include estimated mammographic exam reading times, estimated complexity ratings for images to be read, recommendations or assignments of image readers, job/task scheduling dates/time, etc. For instance, the predictive model may determine that the reading time of breast images having a particular set of breast attributes (e.g., shape, density, lesions, etc.) varies based on the attributes of the image reader and the conditions under which the mammographic exam reading is performed. Based on the determination, the predictive model may use one or more data correlation techniques to determine correlations between known reading times for images and the factors/data points corresponding to the known reading times.

At operation 414, a reading time may be estimated. In aspects, the trained predictive model may use the second set of data to generate one or more outputs. For example, the predictive model may evaluate the second set of data to determine correlations between the data used to train the predictive model and the second set of data. Based on the determined correlations, one or more reading times for a breast image associated with the second set of data may be estimated. For instance, based on identifying that an imaged breast has a BI-RADS mammographic density of Type 2 and no lesions have been identified in the breast image, the predictive model may estimate an mammographic exam reading time of 20 minutes for image readers having less than five years of experience, and an mammographic exam reading time of 10 minutes for image readers having five or more years of experience. In another example, based on the correlations determined by the predictive model, a complexity rating/system may alternately or additionally be estimated/generated. For instance, based on a BI-RADS mammographic density classification, a lesion count, and/or an estimated reading time, the predictive model may estimate an reading complexity for a mammographic exam. Alternately, the predictive model may use the case complexity index generated or updated at operation 406 to estimate a reading complexity. For instance, the predictive model may provide at least a portion of second set of data to the case complexity index. In response, the case complexity index may provide a complexity rating for reading a mammographic exam to the predictive model.

At operation 416, an estimated reading time may be output. In aspects, one or more estimated mammographic exam reading times may be output by the predictive model. The estimated reading time(s) may correspond to an individual image reader, multiple image readers, or one or more categories of readers. For example, an estimated reading time may represent the amount of time an "average" image reader requires to read a mammographic exam. Alternately, each estimated reading time may represent the amount of time that an "average" image reader in a particular category of image readers requires to read a mammographic exam. In some aspects, the predicted reading time may be provided to a healthcare professional via, for example, the user interface described above. Providing the predicted reading time may cause one or more additional actions to be performed. For instance, based on the predicted reading time, one or more radiologists having the expertise and available time to read a mammographic exam may be identified and/or notified. The identification/notification may be accomplished by querying one or more HIS devices for radiologist information, such as reading statistics, availability, education/expertise, experience, etc.

Figure 5A:
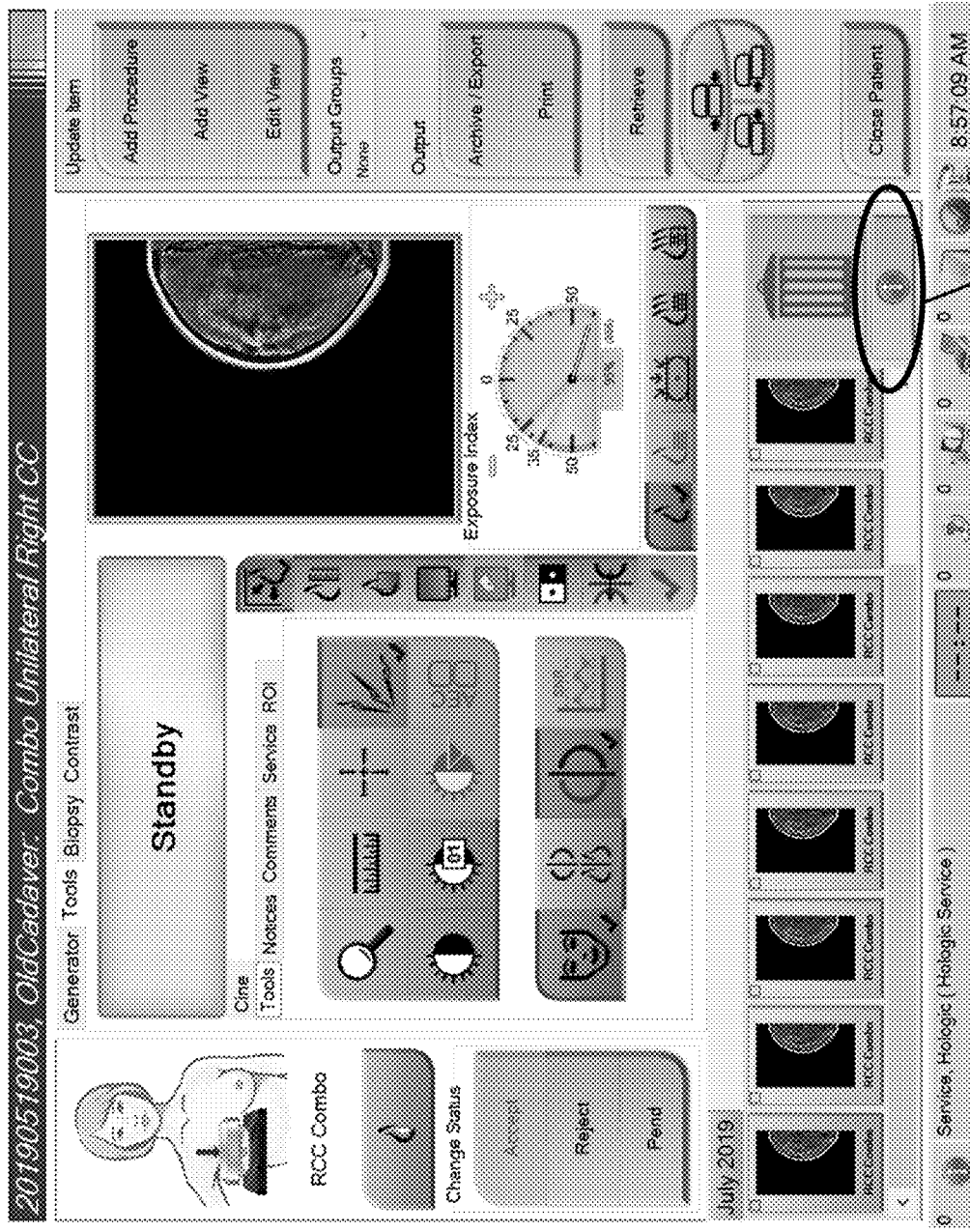
FIG. 5A illustrates an example user interface that is associated with the automated clinical workflow decisions described herein.

FIG. 5A illustrates an example user interface 500 that is associated with the automated clinical workflow decisions described herein. In examples, user interface 500 represents software a technologist uses on a mammography acquisition workstation. The software may be used to collect images during a breast screening exam from an X-ray imaging system, such as X-ray Imaging system 204, and/or to review collected images during a breast screening exam. User interface 500 comprises button 502, which activates an "Analytics" dialog when selected.

Figure 5B:
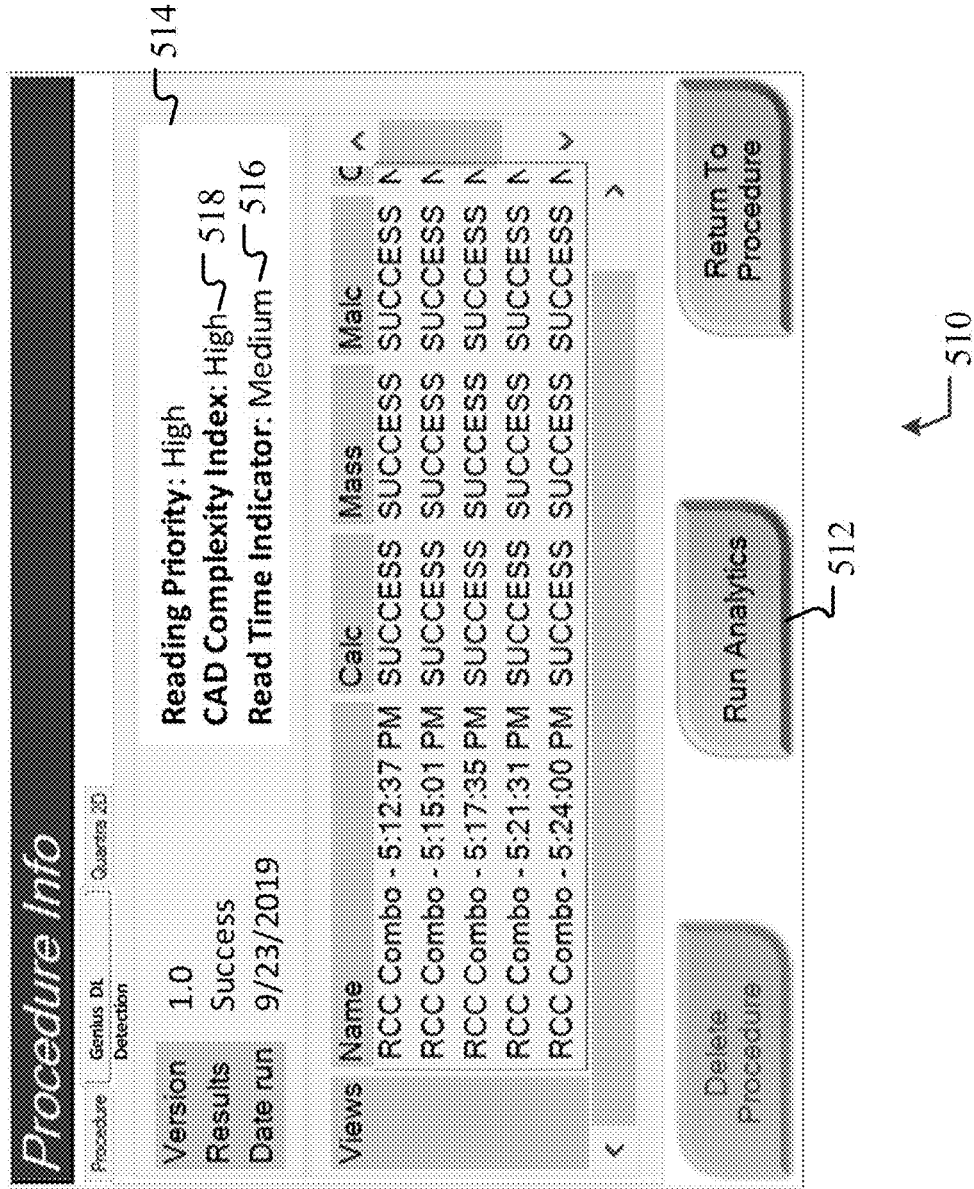
FIG. 5B illustrates an analytics dialog interface associated with the example user interface of FIG. 5A.

FIG. 5B illustrates Analytics dialog 510, which is displayed when button 502 of FIG. 5A is selected. Analytics dialog 510 comprises button 512, analysis result section 514, and reading time indicator 516 and reading complexity indicator 518. In aspects, when button 512 is selected, image evaluation software is launched, and one or more collected images are analyzed using the techniques described in FIG. 3 and FIG. 4. As a result of the analysis, analysis result section 514 is at least partially populated with data, such as reading time indicator 516 and reading complexity indicator 518. In FIG. 5B, reading time indicator 516 indicates that the reading time for the analyzed mammographic exam is "Medium" and reading complexity indicator 518 indicates that the reading complexity for the analyzed mammographic exam is "High." The "Medium" reading time may indicate that an average (or a specific) reader may require a medium or an average amount of time to read the mammographic exam. The "High" complexity may indicate that is difficult to accurately interpret and/or identify one or more aspects of the mammographic exam.

Figure 6:
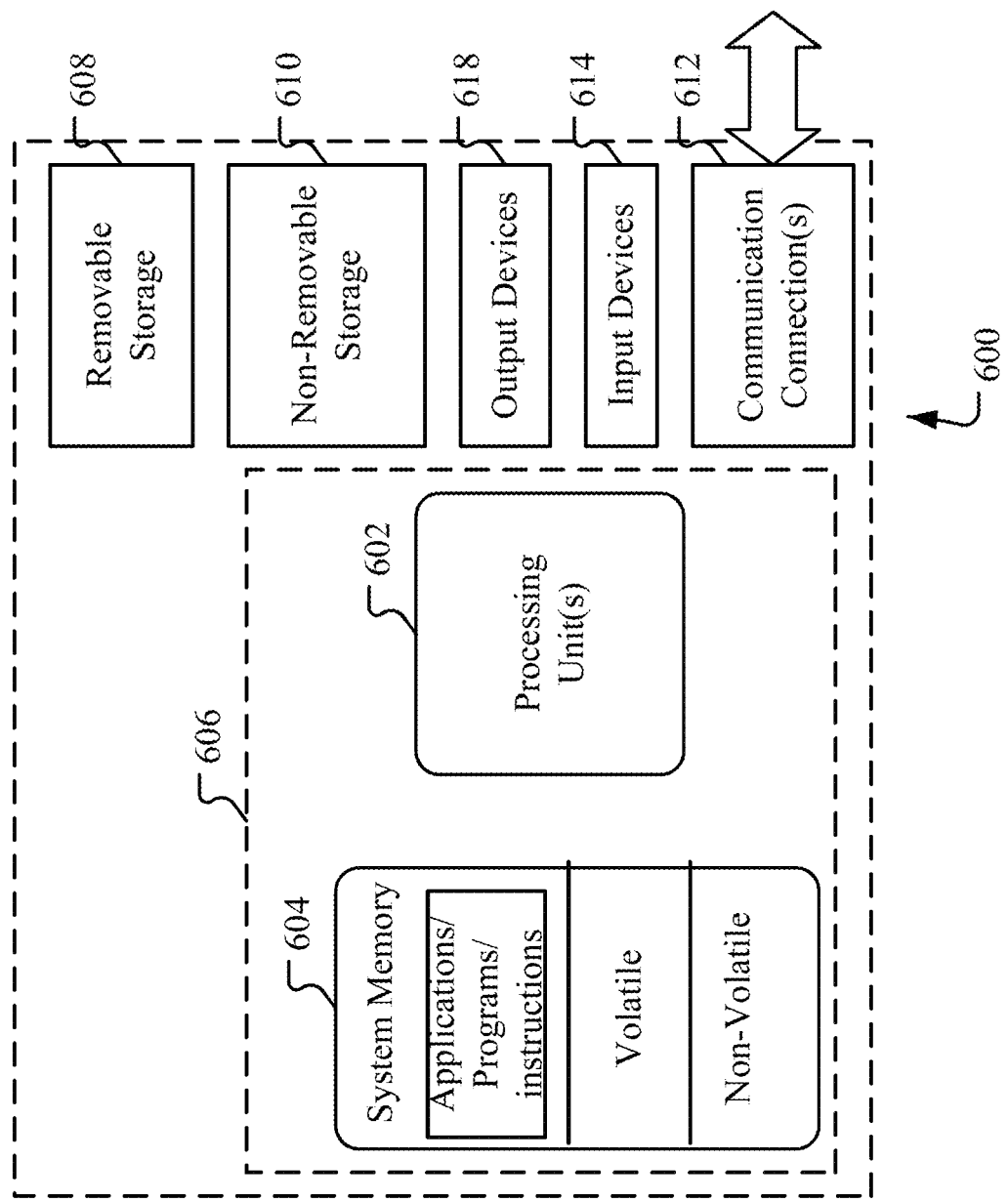
FIG. 6 illustrates one example of a suitable operating environment in which one or more of the present embodiments may be implemented.

FIG. 6 illustrates an exemplary suitable operating environment for detecting X-ray tube output roll off described in FIG. 1. In its most basic configuration, operating environment 600 typically includes at least one processing unit 602 and memory 604. Depending on the exact configuration and type of computing device, memory 604 (storing, instructions to perform the X-ray tube roll off detection techniques disclosed herein) may be volatile (such as RAM), nonvolatile (such as ROM, flash memory, etc.), or some combination of the two. This most basic configuration is illustrated in FIG. 6 by dashed line 606. Further, environment 600 may also include storage devices (removable, 608, and/or non-removable, 610) including, but not limited to, magnetic or optical disks or tape. Similarly, environment 600 may also have input device(s) 614 such as keyboard, mouse, pen, voice input, etc. and/or output device(s) 616 such as a display, speakers, printer, etc. Also included in the environment may be one or more communication connections 612, such as LAN, WAN, point to point, etc. In embodiments, the connections may be operable to facility point-to-point communications, connection-oriented communications, connectionless communications, etc.

Operating environment 600 typically includes at least some form of computer readable media. Computer readable media can be any available media that can be accessed by processing unit 602 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 600 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method of analyzing medical image data, the method comprising:
   receiving, from an X-ray imaging system, mammographic exam data for a patient, wherein the mammographic exam data includes breast image data including one or more X-ray images of the patient's breast tissue;
   processing the breast image data to determine one or more image factors;
   providing the mammographic exam data and the determined one or more image factors to a predictive model;

determining, by the predictive model, correlations between the one or more image factors and training factors, wherein the training factors are determined based at least in part on mammographic exam data for one or more patients and evaluation data for one or more exam readers, wherein determining the correlations comprises evaluating the determined one or more image factors against a complexity index, wherein the complexity index comprises machine learning-generated mappings of a plurality of factors that affect an amount of time required to interpret the mammographic exam data, wherein the plurality of factors include image factors derived from a training set of mammographic exam data and reader factors derived from a training set of evaluation data;

determining an expected reading time for the mammographic exam data based on the correlations;

assigning a complexity label to the breast image data based on at least one of the expected reading time, the correlations, and a portion of the breast image data;

receiving a selection of the mammographic exam data for the patient; and in response to receiving the selection of the mammographic exam data, displaying the complexity label in association with the mammographic exam data.

2. The method of claim 1, wherein the complexity label is assigned according to the complexity index.

3. The method of claim 2, wherein the complexity index comprises a plurality of complexity index ratings that are each mapped to a range of factor values.

4. The method of claim 1, further comprising determining a reading priority based on the correlations.

5. The method of claim 4, further comprising displaying the reading priority in response to the selection of the mammographic exam data.

6. The method of claim 1, further comprising adjusting the expected reading time based on the complexity label assigned.

7. The method of claim 1, further comprising configuring a first workload for a first clinician and a second workload for a second clinician, wherein a first combined reading time of the first workload and a second combined reading time of the second workload differ by less than a threshold amount of time.

8. The method of claim 7, wherein the first workload comprises a first number of exam readings and the second workload comprises a second number of exam readings, and the first number of exam readings differs from the second number of exam readings.

9. The method of claim 1, wherein determining, by the predictive model, the correlations between the one or more image factors and the training factors, includes scoring each of the one or more image factors based on a scoring model.

10. The method of claim 9, wherein the complexity label is associated with a range of scores.

11. The method of claim 10, wherein assigning the complexity label to the breast image data includes determining a total score for the one or more image factors falls within the range of scores.

12. The method of claim 10, wherein assigning the complexity label to the breast image data based on the expected reading time comprises determining the expected reading time falls within a predetermined range, wherein the predetermined range comprises a percentile of aggregated reading time durations.

13. The method of claim 1, wherein the one or more image factors include one or more of a number of regions of interest in the breast image data, a type of region of interest in the breast image data, a number of computer aided design (CAD) marks in the breast image data, a type of CAD marks in the breast image data, a breast evaluation location, a breast density, and a tissue composition.

14. The method of claim 13, wherein processing of the breast image data includes one or more of artifact reduction and de-noising.

15. The method of claim 1, further comprising receiving one or more reader factors, wherein determining the expected reading time for the mammographic exam data is further based on the one or more reader factors.

16. The method of claim 15, wherein the one or more reader factors include factors characterizing an average reader.

17. The method of claim 15, wherein the one or more reader factors and the selection of the mammographic exam data are each associated with a same reader.

18. The method of claim 15, wherein the one or more reader factors includes one or more of a reader experience score, a reader knowledge score, a reader evaluation technique score, and a reader competency score.

19. The method of claim 1, wherein the image factors includes a quantity of factors and the complexity label is associated with a threshold number of factors, and wherein associating the complexity label with the mammographic exam data comprises determining the quantity of factors exceeds the threshold number of factors; and wherein the quantity of factors includes one or more of a number of computer aided design (CAD) marks in the breast image data, a number of CAD marks in a specific portion of the breast image data, or an amount of dense tissue in the breast image data.

20. A system for analyzing medical image data and determining a complexity of the medical image data, the system comprising:

a processor; and memory coupled to the processor, the memory comprising computer executable instructions that, when executed by the processor, performs a method comprising:

receiving, from an X-ray imaging system, mammographic exam data for a patient, wherein the mammographic exam data includes breast image data including one or more X-ray images of the patient's breast tissue;

processing the breast image data to determine one or more image factors;

providing the mammographic exam data and the determined one or more image factors to a predictive model;

determining, by the predictive model, correlations between the one or more image factors and training factors, wherein the training factors are determined based at least in part on mammographic exam data for one or more patients and evaluation data for one or more exam readers, wherein determining the correlations comprises evaluating the one or more image factors against a complexity index, wherein the complexity index comprises machine learning-generated mappings of a plurality of factors that affect an amount of time required to interpret the mammographic exam data, wherein the plurality of factors include image factors derived from a training set of mammographic exam data and reader factors derived from a training set of evaluation data;

determining an expected reading time for the mammographic exam data based on the correlations;

assigning a complexity label to the breast image data based on at least one of the expected reading time, the correlations, and a portion of the breast image data;

receiving a selection of the mammographic exam data for the patient; and in response to receiving the selection of the mammographic exam data, displaying the complexity label in association with the mammographic exam data.

\* \* \* \* \*